United States Patent [19]
Loev

[11] 3,956,325
[45] May 11, 1976

[54] 5-HETEROCYCLIC-1,2,3,6-TETRAHYDRO-4(5H) PYRIMIDINONE

[75] Inventor: Bernard Loev, Broomall, Pa.

[73] Assignee: SmithKline Corporation, Philadelphia, Pa.

[22] Filed: June 6, 1975

[21] Appl. No.: 584,327

Related U.S. Application Data

[62] Division of Ser. No. 435,048, Jan. 21, 1974, Pat. No. 3,910,914.

[52] U.S. Cl. .................. 260/256.4 C; 260/256.5 R; 424/251
[51] Int. Cl.² .............. C07D 239/04; C07D 401/04; C07D 417/04
[58] Field of Search ............... 260/256.4 C, 256.5 R

[56] References Cited
UNITED STATES PATENTS

| | | | |
|---|---|---|---|
| 3,151,114 | 9/1964 | D'Amico et al. | 260/256.5 R |
| 3,681,349 | 8/1972 | Schwan et al. | 260/256.4 C |

*Primary Examiner*—Alton D. Rollins
*Assistant Examiner*—James H. Turnipseed
*Attorney, Agent, or Firm*—Janice E. Williams; Alan D. Lourie; William H. Edgerton

[57] ABSTRACT

The compounds of this invention are 5-heterocyclic-1,2,3,6-tetrahydro-4(5H)-pyrimidinethiones which have pharmacological activity, in particular gastric acid secretion inhibitory activity, and 5-heterocyclic-1,2,3,6-tetrahydro-4(5H)-pyrimidinones which are intermediates in the preparation therefor.

4 Claims, No Drawings

5-HETEROCYCLIC-1,2,3,6-TETRAHYDRO-4(5H) PYRIMIDINONE

This is a division of application Ser. No. 435,048 filed Jan. 21, 1974, now Pat. No. 3,910,914.

This invention relates to new 5-heterocyclic-1,2,3,6-tetrahydro-4(5H)-pyrimidinethiones having pharmacological activity. In particular, these compounds inhibit gastric acid secretion. In addition, this invention relates to new 5-heterocyclic-1,2,3,6-tetrahydro-4(5H)-pyrimidinones which are useful as intermediates in the preparation of the corresponding pyrimidinethiones.

The pyrimidinethione compounds of this invention are represented by the following structural formula:

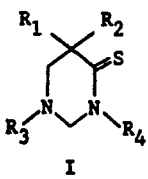

in which:

$R_1$ is 2-pyridyl, 2-pyrimidinyl, 4-pyrimidinyl, 2-pyrazinyl, 2-pyrrolyl, 2-quinolyl, 2-thiazolyl or 4-thiazolyl;

$R_2$ is lower alkyl or phenyl optionally substituted with halogen, lower alkyl or lower alkoxy; and $R_3$ and $R_4$ are hydrogen or lower alkyl or a pharmaceutically acceptable acid addition salt thereof.

The pharmacologically active compounds of this invention have the basic structure for formula I. However, it is apparent to one skilled in the art that well known nuclear substituents such as lower alkyl, lower alkoxy or halogen may be incorporated on the heterocyclic rings. These substituted compounds are used as are the parent compounds.

As used herein, the terms "lower alkyl" and "lower alkoxy" denote groups having from one to four carbon atoms, straight or branched chain; "halogen" denotes chloro, bromo or fluoro.

Preferred compounds of this invention are represented by formula I where $R_1$ is 2-pyridyl. Advantageous compounds are represented by formula I where $R_1$ is 2-pyridyl and $R_2$ is phenyl optionally substituted with halogen, lower alkyl or lower alkoxy.

Particularly preferred in the compound 1,2,3,6-tetrahydro-1-methyl-5-phenyl-5-(2-pyridyl)-4(5H)-pyrimidinethione.

The compounds of formula I produce inhibition of gastric acid secretion. In addition, they show antiarthritic and central nervous system depressant activity.

The inhibition of gastric acid secretion is demonstrated by administration of the compounds of formula I to pylorus ligated rats at doses of about 100 mg./kg. to about 200 mg./kg. orally. In this procedure, compounds which produce an increase in gastric pH or a decrease in the volume of gastric juice or both are considered active.

The compounds of formula I are prepared as shown below:

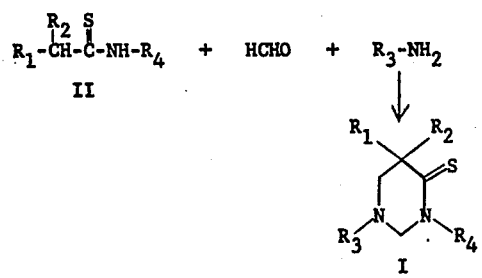

where $R_1$, $R_2$, $R_3$ and $R_4$ are as defined above.

Thus, a 2-substituted-2-heterocyclic thioacetamide is reacted with ammonia or a primary amine and two molar equivalents of formaldehyde. The thioacetamide and/or the ammonia or primary amine may be used in the reaction procedure as the acid addition salt, for example as the hydrochloride or sulfate salt. The reaction may be carried out in aqueous solution but is preferably carried out in an alcoholic solution, for example in methanol or ethanol. The reaction is preferably run at about ambient temperature (ca. 25°C.) to about 100°C.

When $R_4$ is hydrogen, the heterocyclic thioacetamide starting materials (II) are known to the art or are prepared, for example, by reacting the corresponding substituted acetonitrile ($R_1R_2CH$—CN) with hydrogen sulfide in the presence of a base such as an amine or by reacting with ammonium polysulfide. The substituted acetonitriles may be prepared from substituted ketones or carboxyaldehydes ($R_1R_2CO=O$) by replacing to the corresponding alcohol using a reducing agent such as sodium borohydride, then treating the alcohol with a chlorinating agent such as thionyl chloride and treating the resulting chloride with an alkali metal cyanide such as sodium or potassium cyanide.

When $R_4$ is lower alkyl, the heterocyclic thioacetamides (II) not known to the art are prepared by reacting a substituted methyl heterocycle ($R_1R_2CH_2$) with a base such as phenyl or butyl lithium and then with an appropriate isothiocyanate ($R_4'NCS$ where $R_4'$ is lower alkyl) to give the N-substituted 2-substituted-2-heterocyclic thioacetamides. These compounds are also prepared by treatment of the corresponding heterocyclic thioamide where $R_4$ is hydrogen with an N-alkyl amine ($R_4'NH_2$ where $R_4'$ is lower alkyl).

Alternatively, the compounds of formula II are prepared by treatment of the corresponding acetamides with phosphorus pentasulfide in a solvent such as benzene.

A further aspect of this invention is the 5-heterocyclic-1,2,3,6-tetrahydro-4(5H)-pyrimidinones represented by the following structural formula:

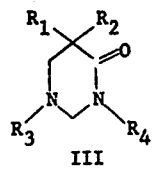

in which:

$R_1$ is pyridyl, 2-pyrimidinyl, 4-pyrimidinyl, 2-pyrazinyl, 2-pyrrolyl, 2-quinolyl, 2-thiazolyl or 4-thiazolyl;

$R_2$ is lower alkyl or phenyl optionally substituted with halogen, lower alkyl or lower alkoxy; and $R_3$ and $R_4$ are hydrogen or lower alkyl or a pharmaceutically acceptable acid addition salt thereof.

Preferred and advantageous compounds of formula III are those used in preparing the corresponding preferred and advantageous compounds of formula I. Particularly preferred is the compound 1,2,3,6-tetrahydro-1-methyl-5-phenyl-5-(2-pyridyl)-4(5H)-pyrimidinone.

The pyrimidinones represented by formula III are useful as intermediates in the preparation of the corresponding pyrimidinethiones of formula I by treatment of the compounds of formula III with phosphorus pentasulfide in a solvent such as benzene. The pyrimidinones are prepared by condensation of an acetamide corresponding to a thioacetamide of formula II with formaldehyde and ammonia or a primary amine as previously described.

The pharmaceutically acceptable, acid addition salts of the compounds of this invention are formed with organic and inorganic acids by methods known to the art. For example, the base is reacted with an organic or inorganic acid in an aqueous miscible solvent, such as acetone or ethanol, with isolation of the salt by concentration and cooling or in an aqueous immiscible solvent, such as ethyl ether or chloroform, with the desired salt separating directly. Exemplary of the salts which are included in this invention are maleate, fumarate, succinate, oxalate, benzoate, methanesulfonate, ethanedisulfonate, benzenesulfonate, acetate, propionate, tartrate, citrate, camphorsulfonate, hydrochloride, hydrobromide, sulfate, sulfamate, phosphate and nitrate salts.

The compounds of formula I are administered internally either parenterally, rectally or, preferably, orally in an amount to produce the desired biological activity.

Preferably, the compounds are administered in conventional dosage forms prepared by combining an appropriate dose of the compound with standard pharmaceutical carriers.

The pharmaceutical carrier may be for example a solid or a liquid. Exemplary of solid carriers are lactose, magnesium stearate, terra alba, sucrose, talc, stearic acid, gelatin, agar, pectin, acacia or cocoa butter. The amount of solid carrier will vary widely but preferably will be from about 25 mg. to about 1 gm. Exemplary of liquid carriers are syrup, peanut oil, olive oil, sesame oil, propylene glycol, polyethylene glycol (mol. wt. 200–400) and water. The carrier or diluent may include a time delay material well known in the art such as, for example, glyceryl monostearate or glyceryl distearate alone or with a wax.

A wide variety of pharmaceutical forms can be employed, for example the preparation may take the form of tablets, capsules, powders, suppositories, troches, lozenges, syrups, emulsions, sterile injectable liquids or liquid suspensions or solutions.

The pharmaceutical compositions are prepared by conventional techniques involving procedures such as mixing, granulating and compressing or dissolving the ingredients as appropriate to the desired preparation.

It will be apparent to one skilled in the art that the compounds of this invention have no asymmetric carbon atom and thus optical isomers may be present. The connotation of the formulas presented herein is to include all isomers, the separated forms as well as mixtures thereof.

The following examples are not limiting but are illustrative of the compounds of this invention and the processes for their preparation. Temperatures are in degrees Centigrade unless otherwise indicated.

EXAMPLE 1

A. To a mixture of 10.0 g. of 2-phenyl-2-(2-pyridyl)-thioacetamide and 4.5 g. of methylamine hydrochloride in 200 ml. of methanol is added 7 ml. of 37% formaldehyde solution. The reaction mixture is stirred at 25° for 18 hours then the precipitated 1,2,3,6-tetrahydro-1-methyl-5-phenyl-5-(2-pyridyl)-4(5H)-pyrimidinethione hydrochloride is collected by filtration and recrystallized from ethanol, m.p. 264°–267°. Treatment of a solution of the salt in water with 5% aqueous sodium carbonate until basic gives 1,2,3,6-tetrahydro-1-methyl-5-phenyl-5-(2-pyridyl)-4(5H)-pyrimidinethione, m.p. 138°–140°.

B. A solution of 14.0 g. of 2-phenyl-2-(2-pyridyl)acetamide in 200 ml. of methanol is treated with 6.75 g. of methyl amine hydrochloride and 4.0 g. of 37% formaldehyde solution. The reaction mixture is stirred for 12 hours at 25° then filtered to remove the product 1,2,3,6-tetrahydro-1-methyl-5-phenyl-5-(2-pyridyl)-4(5H)-pyrimidinone hydrochloride, m.p. 170°–173°. Treatment of a solution of the salt in water with 5% aqueous sodium carbonate until basic gives 1,2,3,6-tetrahydro-1-methyl-5-phenyl-5-(2-pyridyl)-4(5H)-pyrimidinone.

To a solution of 1,2,3,6-tetrahydro-1-methyl-5-phenyl-5-(2-pyridyl)-4(5H)-pyrimidinone in benzene is added 0.16 equivalent of phosphorus pentasulfide. The reaction mixture is heated gently for 30 minutes then water is added and the layers are separated. The aqueous layer is extracted again with benzene and the organic layers are combined, washed with water, dried (MgSO$_4$) and concentrated in vacuo to give 1,2,3,6-tetrahydro-1-methyl-5-phenyl-5-(2-pyridyl)-4(5H)-pyrimidinethione.

EXAMPLE 2

To a solution of 30 g. of 2-phenyl-2-(2-pyridyl)acetamide in 500 ml. of methanol is added 11.1 g. of ammonium chloride and 45 ml. of 37% formaldehyde solution. The reaction mixture is brought to reflux and stirred for 12 hours. The mixture is then cooled and the methanol is removed in vacuo. Hot water (400 ml.) is added to the residue and the aqueous solution is made basic with 5% aqueous sodium carbonate. The resulting mixture is extracted with chloroform and the extract is washed with water and saturated sodium chloride solution, dried (MgSO$_4$) and concentrated to give 1,2,3,6-tetrahydro-5-phenyl-5-(2-pyridyl)-4(5H)-pyrimidinone as an oil which crystallizes upon trituration with ethyl acetate, m.p. 201°–203°.

Treatment of 1,2,3,6-tetrahydro-5-phenyl-5-(2-pyridyl)-4(5H)-pyrimidinone with phosphorus pentasulfide as described in the procedure of Example 1 gives 1,2,3,6-tetrahydro-5-phenyl-5(2-pyridyl)-4(5H)-pyrimidinethione.

EXAMPLE 3

By the procedure of Example 1, using the following thioacetamides in place of 2-phenyl-2-(2-pyridyl)thioacetamide:

2-phenyl-2-(2-pyrazinyl)thioacetamide
2-(4-chlorophenyl)-2-(2-pyrimidinyl)thioacetamide
2-phenyl-2-(2-thiazolyl)thioacetamide the final products are, respectively:

1,2,3,6-tetrahydro-1-methyl-5-phenyl-5-(2-pyrazinyl)-4(5H)-pyrimidinethione 5-(4-chlorophenyl)-1,2,3,6-tetrahydro-1-methyl-5-(2-pyrimidinyl)-4(5H)-pyrimidinethione
1,2,3,6-tetrahydro-1-methyl-5-phenyl-5-(2-thiazolyl)-4(5H)-pyrimidinethione.

EXAMPLE 4

Substitution of the following 2-substituted phenyl-2-(2-pyridyl)thioacetamides:
2-(4-chlorophenyl)-2-(2-pyridyl)thioacetamide
2-(2-fluorophenyl)-2-(2-pyridyl)thioacetamide
2-(4-methoxyphenyl)-2-(2-pyridyl)thioacetamide
2-(3-methylphenyl)-2-(2-pyridyl)thioacetamide
in the procedure of Example 1 for 2-phenyl-2-(2-pyridyl)thioacetamide gives the following compounds of this invention, respectively:
5-(4-chlorophenyl)-1,2,3,6-tetrahydro-1-methyl-5-(2-pyridyl)-4(5H)-pyrimidinethione
5-(2-fluorophenyl)-1,2,3,6-tetrahydro-1-methyl-5-(2-pyridyl)-4(5H)-pyrimidinethione
1,2,3,6-tetrahydro-5-(4-methoxyphenyl)-1-methyl-5-(2-pyridyl)-4(5H)-pyrimidinethione
1,2,3,6-tetrahydro-1-methyl-5-(3-methylphenyl)-5-(2-pyridyl)pyrimidinethione.

EXAMPLE 5

When an equivalent amount of a thioamide listed below:
3-methyl-2-(2-pyridyl)thiobutanamide
2-(2-pyridyl)thiobutanamide
2-(2-pyridyl)thiopentanamide
2-(2-pyridyl)thiohexanamide
2-(2-pyrazinyl)thiobutanamide
is substituted in the procedure of Example 1 for 2-phenyl-2-(2-pyridyl)thioacetamide the following compounds are obtained, respectively:
1,2,3,6-tetrahydro-1-methyl-5-isopropyl-5-(2-pyridyl)-4(5H)-pyrimidinethione
5-ethyl-1,2,3,6-tetrahydro-1-methyl-5-(2-pyridyl)-4(5H)-pyrimidinethione
1,2,3,6-tetrahydro-1-methyl-5-n-propyl-5-(2-pyridyl)-4(5H)-pyrimidinethione
5-n-butyl-1,2,3,6-tetrahydro-1-methyl-5-(2-pyridyl)-4(5H)-pyrimidinethione
5-ethyl-1,2,3,6-tetrahydro-1-methyl-5-(2-pyrazinyl)-4(5H)-pyrimidinethione.

EXAMPLE 6

Methyl 4-thiazolyl ketone (12.7 g.) is added to 3.8 g. of sodium borohydride in 100 ml. of isopropanol and the mixture is heated at reflux for four hours. Dilute hydrochloric acid (100 ml.) is added and the mixture is evaporated to dryness. The residue is dissolved in a small volume of water and the aqueous solution is made basic with 5% aqueous sodium bicarbonate solution, then evaporated to dryness. The residue is extracted with ether and the ether is removed from the extract in vacuo to give α-(4-thiazolyl)ethanol.

A mixture of 8.4 g. of α-(4-thiazolyl)ethanol and 25 ml. of thionyl chloride is heated for four hours on a steam bath, then concentrated in vacuo. The residue is dissolved in water and basified with 5% aqueous sodium carbonate solution. Extracting with ether, then drying and concentrating the extracts gives 4-(α-chloroethyl)thiazole.

A solution of 7.8 g. of 4-(α-chloroethyl)thiazole is added dropwise to a suspension of 5.2 g. of sodium cyanide in 100 ml. of dimethylsulfoxide. The mixture is heated at 50° for two hours, then diluted with 150 ml. of a 5% aqueous sodium carbonate solution and extracted with ether. The extract is dried and concentrated to give α-(4-thiazolyl)propionitrile.

To 12.4 g. of α-(4-thiazolyl)propionitrile in 13 ml. of pyridine is added 5 ml. of triethylamine. Hydrogen sulfide is bubbled into the mixture for two hours. The mixture is heated in a sealed tube at 100° for 15 hours, then cooled and concentrated to dryness. The residue is extracted with chloroform and the extract is concentrated to dryness. The residue is crystallized from chloroform-hexane to give 2-(4-thiazolyl)thiopropanamide.

Using 2-(4-thiazolyl)thiopropanamide in place of 2-phenyl-2-(2-pyridyl)thioacetamide in the procedure of Example 1, the product is 1,2,3,6-tetrahydro-1,5-dimethyl-5-(4-thiazolyl)-4(5H)-pyrimidinethione.

EXAMPLE 7

By substitution of an equivalent amount of methyl 4-pyrimidinyl ketone, methyl 2-pyrrolyl ketone or methyl 2-quinolyl ketone in the procedure of Example 6 for methyl 4-thiazolyl ketone followed by the subsequent synthetic steps described therein, there are prepared the following thiopropanamides:
2-(4-pyrimidinyl)thiopropanamide
2-(2-pyrrolyl)thiopropanamide
2-(2-quinolyl)thiopropanamide.

Substitution of a thiopropanamide listed above in the procedure of Example 1 for 2-phenyl-2-(2-pyridyl)thioacetamide gives the following compounds of this invention, respectively:
1,2,3,6-tetrahydro-1,5-dimethyl-5-(4-pyrimidinyl)-4(5H)-pyrimidinethione
1,2,3,6-tetrahydro-1,5-dimethyl-5-(2-pyrrolyl)-4(5H)-pyrimidinethione
1,2,3,6-tetrahydro-1,5-dimethyl-5-(2-quinolyl)-4(5H)-pyrimidinethione.

EXAMPLE 8

When ethylamine, isopropylamine, n-butylamine or t-butylamine or a corresponding hydrochloride salt is substituted in the procedure of Example 1 for methylamine hydrochloride, there are ultimately obtained the following pyrimidinethiones:
1-ethyl-1,2,3,6-tetrahydro-5-phenyl-5-(2-pyridyl)-4(5H)-pyrimidinethione
1,2,3,6-tetrahydro-5-phenyl-1-isopropyl-5-(2-pyridyl)-4(5H)-pyrimidinethione
1-n-butyl-1,2,3,6-tetrahydro-5-phenyl-5-(2-pyridyl)-4(5H)-pyrimidinethione
1-t-butyl-1,2,3,6-tetrahydro-5-phenyl-5-(2-pyridyl)-4(5H)-pyrimidinethione.

EXAMPLE 9

2-Benzylpyridine (6.1 g.) dissolved in 25 ml. of dry benzene is added dropwise to 20 ml. of 2M phenyl lithium in benzene/ether with cooling. The mixture is stirred for 30 minutes, then 2.6 g. of methyl isothiocyanate, dissolved in 40 ml. of dry benzene, is added dropwise with cooling. The resulting solution is stirred overnight. An equal volume of water is added and the solution is cooled and made acidic with 10% aqueous hydrochloric acid. The phases are separated, the organic phase is washed with water and the combined aqueous phases are made basic to about pH 9, then extracted with chloroform. The chloroform extracts are washed with water and dried over magnesium sulfate. Filtration and removal of solvent gives a residue which is recrystallized from isopropyl ether/ethanol to give N-methyl- 2-phenyl-2-(2-pyridyl)thioacetamide.

Substitution of N-methyl-2-phenyl-2-(2-pyridyl)thioacetamide in the procedure of Example 1 for 2-phenyl-2-(2-pyridyl)thioacetamide gives 1,2,3,6-tetrahydro-1,3-dimethyl-5-phenyl-5-(2-pyridyl)-4(5H)-pyrimidinethione.

EXAMPLE 10

Using, in the procedure of Example 9, the following isothiocyanates in place of methyl isothiocyanate:
ethyl isothiocyanate
n-propyl isothiocyanate
t-butyl isothiocyanate
the following thioacetamides are obtained:
N-ethyl-2-phenyl-2-(2-pyridyl)thioacetamide
2-phenyl-N-n-propyl-2-(2-pyridyl)thioacetamide
N-t-butyl-2-phenyl-2-(2-pyridyl)thioacetamide.

Reacting with the above prepared thioacetamides with methylamine hydrochloride and formaldehyde by the procedure described in Example 1 gives the following products, respectively:
3-ethyl-1,2,3,6-tetrahydro-1-methyl-5-phenyl-5-(2-pyridyl)-4(5H)-pyrimidinethione
1,2,3,6-tetrahydro-1-methyl-5-phenyl-3-n-propyl-5-(2-pyridyl)-4(5H)-pyrimidinethione
3-t-butyl-1,2,3,6-tetrahydro-1-methyl-5-phenyl-5-(2-pyridyl)-4-(5H)-pyrimidinethione.

EXAMPLE 11

When a thioacetamide listed in Example 10 is reacted with formaldehyde and ethylamine, isopropylamine, n-butylamine or t-butylamine, or a corresponding hydrochloride salt, according to the procedure of Example 1, there are obtained the following compounds of this invention, respectively:
1,3-diethyl-1,2,3,6-tetrahydro-5-phenyl-5-(2-pyridyl)-4(5H)-pyrimidinethione
3-ethyl-1,2,3,6-tetrahydro-5-phenyl-1-isopropyl-5-(2-pyridyl)-4(5H)-pyrimidinethione
1-n-butyl-3-ethyl-1,2,3,6-tetrahydro-5-phenyl-5-(2-pyridyl)-4(5H)-pyrimidinethione
1-t-butyl-3-ethyl-1,2,3,6-tetrahydro-5-phenyl-5-(2-pyridyl)-4(5H)-pyrimidinethione
1-ethyl-1,2,3,6-tetrahydro-5-phenyl-3-n-propyl-5-(2-pyridyl)-4(5H)-pyrimidinethione
1,2,3,6-tetrahydro-5-phenyl-1-isopropyl-3-n-propyl-5-(2-pyridyl)-4(5H)-pyrimidinethione
1-n-butyl-1,2,3,6-tetrahydro-5-phenyl-3-n-propyl-5-(2-pyridyl)-4(5H)-pyrimidinethione
1-t-butyl-1,2,3,6-tetrahydro-5-phenyl-3-n-propyl-5-(2-pyridyl)-4(5H)-pyrimidinethione
3-t-butyl-1-ethyl-1,2,3,6-tetrahydro-5-phenyl-5-(2-pyridyl)- 4(5H)-pyrimidinethione
3-t-butyl-1,2,3,6-tetrahydro-5-phenyl-1-isopropyl-5-(2-pyridyl)-4(5H)-pyrimidinethione
1-n-butyl-3-t-butyl-1,2,3,6-tetrahydro-5-phenyl-5-(2-pyridyl)-4(5H)-pyrimidinethione
1,3-di-t-butyl-1,2,3,6-tetrahydro-5-phenyl-5-(2-pyridyl)-4(5H)-pyrimidinethione.

EXAMPLE 12

To 1 g. of 1,2,3,6-tetrahydro-1-methyl-5-phenyl-5-(2-pyridyl)-4(5H)-pyrimidinethione in ether is added hydrogen bromide in ether to give the hydrobromide salt.

EXAMPLE 13

One gram of 1,2,3,6-tetrahydro-1-methyl-5-phenyl-5-(2-pyridyl)-4(5H)-pyrimidinethione in ethanol is treated with an equimolar amount of maleic acid in ethanol. The solvent is removed in vacuo to give the maleate salt.

In like manner, using oxalic acid, the oxalate salt of 1,2,3,6-tetrahydro-1-methyl-5-phenyl-5-(2-pyridyl)-4(5H)-pyrimidinethione is prepared.

EXAMPLE 14

| Ingredients | Amount |
| --- | --- |
| 1,2,3,6-Tetrahydro-1-methyl-5-phenyl-5-(2-pyridyl)-4(5H)-pyrimidinethione | 400 mg. |
| Lactose | 100 mg. |

The above ingredients are mixed and filtered into a hard gelatin capsule.

In a similar manner, the other pyrimidinethione compounds of this invention disclosed above may be formulated into capsules.

What is claimed is:
1. A compound of the formula:

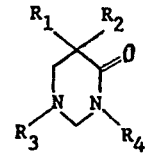

in which:
R₁ is 2-pyridyl, 2-pyrimidinyl, 4-pyrimidinyl, 2-pyrazinyl, 2-pyrrolyl, 2-quinolyl, 2-thiazolyl or 4-thiazolyl;
R₂ is lower alkyl or phenyl optionally substituted with halogen, lower alkyl or lower alkoxy; and
R₃ and R₄ are hydrogen or lower alkyl
or a pharmaceutically acceptable acid addition salt thereof.

2. A compound according to claim 1 in which R₁ is 2-pyridyl.

3. A compound according to claim 2 in which R₂ is phenyl optionally substituted with halogen, lower alkyl or lower alkoxy.

4. A compound according to claim 3 being the compound 1,2,3,6-tetrahydro-1-methyl-5-phenyl-5-(2-pyridyl)-4(5H)-pyrimidinone.

* * * * *

UNITED STATES PATENT AND TRADEMARK OFFICE
CERTIFICATE OF CORRECTION

PATENT NO. : 3,956,325
DATED : May 11, 1976
INVENTOR(S) : Bernard Loev

It is certified that error appears in the above—identified patent and that said Letters Patent are hereby corrected as shown below:

Column 1, line 39, "for" should read -- of -- .

Column 2, line 31, "replacing" should read -- reducing --.

Signed and Sealed this

Seventh Day of September 1976

[SEAL]

Attest:

RUTH C. MASON
Attesting Officer

C. MARSHALL DANN
Commissioner of Patents and Trademarks